United States Patent [19]

Chauvin et al.

[11] 4,283,305

[45] Aug. 11, 1981

[54] CATALYST COMPOSITION AND ITS USE FOR OLIGOMERIZING OLEFINS

[75] Inventors: Yves Chauvin, Le Pecq; Dominique Commereuc, Meudon; Jean Gaillard, Lyons; Gerard Leger, Saint Genis les Ollieres; Nhu Hung Phung, Antony, all of France

[73] Assignee: Institut Francais du Petrole, Rueil-Malmaison, France

[21] Appl. No.: 102,488

[22] Filed: Dec. 11, 1979

[30] Foreign Application Priority Data

Dec. 11, 1978 [FR] France ............................ 78 35011

[51] Int. Cl.$^3$ ..................... B01J 31/14; B01J 31/04
[52] U.S. Cl. ......................... 252/431 C; 252/431 R; 585/512; 585/523
[58] Field of Search .................. 252/431 R, 431 C

[56] References Cited

U.S. PATENT DOCUMENTS

| | | | |
|---|---|---|---|
| 3,542,695 | 11/1970 | Dawans et al. | 252/431 C |
| 3,728,283 | 4/1973 | Chauvin et al. | 252/43 R X |
| 3,928,303 | 12/1975 | Yasui et al. | 252/431 C X |
| 3,937,745 | 2/1976 | Wideman et al. | 252/431 C X |

*Primary Examiner*—Patrick Garvin
*Attorney, Agent, or Firm*—Millen & White

[57] ABSTRACT

Catalyst composition for oligomerizing olefins, obtained by contacting (a) a bivalent nickel compound with (b) a hydrocarbylaluminum compound of the formula AlRCl$_2$ where R is a monovalent hydrocarbon radical, and (c) a Bronsted acid consisting preferably of a halogenocarboxylic acid of the formula R$_1$COOH in which R$_1$ is a halogenoalkyl radical of the formula C$_m$H$_p$X$_q$, X being halogen, m an integer from 1 to 3, p being zero or an integer and q being an integer, the condition $p+q=2m+1$ being fulfilled. A preferred Bronsted acid is of the formula R$_2$COOH in which R$_2$ is a halogenomethyl group of the formula CX$_n$H$_{3-n}$, X being halogen and n an integer from 1 to 3.

9 Claims, No Drawings

CATALYST COMPOSITION AND ITS USE FOR OLIGOMERIZING OLEFINS

BACKGROUND OF THE INVENTION

This invention concerns a new catalyst composition and its use for oligomerizing, particularly dimerizing and trimerizing, monoolefins. More particularly, it relates to combinations obtained by contacting, in any order, at least one bivalent nickel compound with at least one aluminum hydrocarbyl halide and at least one Bronsted organic acid.

It is already known to manufacture catalysts for dimerizing or codimerizing monoolefins such as ethylene, propylene or n-butenes. Among these catalysts, the following have been particularly described: the products formed by interacting $\pi$-allyl nickel phosphine halides with Lewis acids (French Patent No. 1,410,430), the products formed by interacting phosphine nickel halides with Lewis acids (U.S. Pat. No. 3,485,881) and the products obtained by interacting certain nickel caboxylates with hydrocarbylaluminum halides (U.S. Pat. No. 3,321,546). Almost all of these catalysts are used in the presence of a ligand such as a phosphorus organic compound. As a matter of fact, it is desirable to make available oligomerization catalysts free of phosphorus. Other catalysts make use of zerovalent nickel compounds which are not of a very practical use in view of their instability and their high cost.

It has also been proposed to make use of catalysts wherein nickel is deposited on an inorganic carrier with acid sites, for example silica, silica-alumina, aluminum phosphate. These catalysts are in the solid phase, in contrast with the liquid phase catalysts according to the invention. Their activity is weak.

Finally, the prior art technique suffers from the following drawback: the continuous industrial operation of the known catalyst compositions for the treatment of olefin cuts such as those produced by petrochemical processes as the catalytic cracking or the steamcracking, raises some difficulties resulting, on the one hand, from the impurities contained in the cuts and, in the other hand, from an effective activity which is often smaller than in a closed vessel wherein all the constituents are introduced simultaneously at the beginning of the reaction and from the fact that said activity decreases with time.

DETAILED DISCUSSION

It has been observed unexpectedly that the combination of a bivalent nickel compound with an aluminum hydrocarbyl halide and a Bronsted acid compound leads to a catalyst composition which, particularly in a continuous process, has a better activity than the prior ones, retains a greater stability during time and is less sensitive to impurities which are present as traces in olefinic charges.

As nickel compound there may be used any of the bivalent nickel compounds, preferably those soluble in a proportion of more than one gram per liter in a hydrocarbon medium (example: in n-heptane at 20° C.) and more particularly in the reactants or the reaction medium, and preferably the carboxylates of the general formula $(R_3COO)_2Ni$ where $R_3$ is a hydrocarbon radical, for example alkyl, cycloalkyl, alkenyl, aryl, aralkyl or alkaryl containing up to 20 carbon atoms, preferably a hydrocarbyl radical of from 5 to 20 carbon atoms. The two radicals $R_3$ may also consist of an alkylene radical having from 6 to 18 carbon atoms. Examples of nickel compounds are bivalent nickel salts as follows: octoate, 2-ethyl hexanoate, decanoate, stearate, oleate, salicylate, acetylacetonate, hydroxydecanoate. A number of further examples may be found in publications and patents and the invention is not limited to the above-mentioned examples.

The radical $R_3$ may be substituted with 1 to 4 (or more) halogen atoms, hydroxy, ketone, nitro, cyano groups or other groups which do not impede the reaction.

The hydrocarbylaluminum halide compounds comply with the general formula $AlRCl_2$ wherein R is a hydrocarbon group containing for example up to 12 carbon atoms, such as alkyl, aryl, aralkyl, alkaryl or cycloalkyl. As examples of such compounds there can be mentioned, dichloroethylaluminum and dichloroisobutylaluminum.

The Bronsted acid is a compound of the formula HZ wherein Z is an organic anion, for example, carboxylate, sulfonate or phenolate. The preferred acids have a $pK_a$ at 20° C. at most equal to 3, they are preferably selected from those which are soluble in the nickel compound or in its solution in a hydrocarbon or another convenient solvent, at the desired concentration, and which do not contain phosphorus. A category of acids which is preferred includes halogenocarboxylic acids of formula $R_1COOH$ wherein $R_1$ is a haloalkyl radical, particularly one of those containing at least one halogen atom in the position with respect to the COOH group, with a total from 2 to 10 carbon atoms. A category of acids which is preferred includes the halogeno carboxylic acids of formula $R_1COOH$ wherein $R_1$ is a halogenoalkyl radical containing from 1 to 3 carbon atoms, having the formula $C_mH_pX_q$ wherein X is halogen (fluorine, chlorine, bromine or iodine), m=1, 2 or 3, p is zero or an integer and q is an integer, provided that the following relationship $p+q=2m+1$ is observed. More advantageously, there is used a halogenoacetic acid of the formula $R_2COOH$ wherein $R_2$ is a halogenomethyl group of the formula $CX_nH_{3-n}$ in which X is fluorine, chlorine, bromine or iodine, n being an integer from 1 to 3. As acids which can be used, there can be mentioned the trifluoroacetic, difluoroacetic, monofluoroactic, trichloroacetic, dichloroacetic, monochloroacetic, tribromoacetic, dibromoacetic, monobromoacetic, triiodoacetic, diiodoacetic, monoiodoacetic, pentafluoropropionic, 2-fluoro propionic, 2,2-dichloropropionic, 2-chloro propionic, heptafluorobutyric, 2-fluorobutyric or 2-chloro-butyric acids. The preceding examples are not limitative. Other acids can be used, such for examples as arylsulfonic, alkylsulfonic, picric, nitroacetic, dinitrobenzoic, orthonitrobenzoic and cyanacetic acids.

The invention has also for object a process for oligomerizing monoolefins in the presence of a catalyst system as above described at a temperature from $-20°$ C. to $+60°$ C. under such pressure conditions that the reactants be maintained, at least in their major part, in liquid phase or condensed phase.

The monoolefins available to be dimerized or oligomerized are, for example, ethylene, propylene, n-butenes, n-pentenes either pure or as mixtures issued from synthesis processes such as catalytic cracking. They may be co-oligomerized between themselves or with isobutene, for example ethylene with propylene and n-butenes, propylene with n-butenes, n-butenes with isobutene The concentration, expressed as nickel, of the catalyst composition in the liquid phase of the oligomerization reaction is usually from 5 to 500 parts per million of parts by weight. The molar ratio of the hydrocarbyl aluminum halide to the nickel compound is usually from 1:1 to 50:1 and more advantageously from 2:1 to 20:1. The molar ratio of the Bronsted acid to the aluminum compound is advantageously from 0.001:1 to 1:1, preferably from 0.01:1 to 0.5:1; the preferred value of the molar ratio of the Bronsted acid to the nickel compound is from 0.25:1 to 5:1.

The process may be carried out in a reactor with one or more reaction stages in series, the olefin charge and/or the constituents of the catalyst system being introduced continuously either in the first stage or in the first and in any one of the other stages. It is also possible to introduce in the second and/or "$n^{th}$" stage only 1 or 2 constituents of the catalyst mixture.

At the outlet of the reactor, the catalyst may be deactivated, for example by means of ammonia and/or a sodium hydroxide aqueous solution and/or an aqueous solution of sulfuric acid. The unconverted olfins and the alkanes are then separated from the oligomers by distillation. The products obtained by the above process may be used as components of motor-fuel or as feed charge in a hydroformylation process for the synthesis of aldehydes and alcohols.

The following examples are given by way of illustration and are not intended to limit in any way the scope of the invention.

COMPARATIVE EXAMPLE NO. 1

This example forms no part of the invention but is destined to show the advantages thereof by comparison with the prior art.

The oligomerization reactor consists of a cylindrical vessel made of steel, coupled with an external recirculation system operated at a flow rate of 2 m$^3$/h, destined to ensure the homogeneity of the reaction mixture, and with a heat exchanger. The total reaction volume is 7.2 liters. In the recirculation system there is introduced 1 kg/h of a $C_3$ cut issued from a catalytic cracking unit and containing about 70% by weight of propylene and 30% of propane, 0.33 g/h of dichloro-ethylaluminum as a solution in isooctane and 0.1 g/h of a $C_9$–$C_{13}$ nickel carboxylate having a 10% metal content, as a solution in isooctane. The pressure in the reactor is maintained at 15 bars by continuous withdrawal of the reaction product and the temperature is maintained at 42° C. by controlling the flow rate through the exchanger.

After 3 days of run, the conversion of propylene to a mixture consisting mainly of dimers and trimers is stabilized at 70%. Taking into account the recovered propylene, the yield of propylene dimers and trimers amounts to 97%.

EXAMPLE NO. 2

In the same apparatus as in example 1, and with the same operating conditions, there is introduced, at the same flow rates, the $C_3$ cut and the catalyst components with the exception that the nickel carboxylate solution contained trifluoroacetic acid at such a concentration as to correspond to a flow rate of 0.02 g/h. After 3 days of run, the propylene conversion to an oligomer mixture was maintained at 91%, said mixture being substantially identical to that of the preceding example. The yield was 97% as in example 1.

COMPARATIVE EXAMPLE NO. 3

The oligomerization plant comprises 2 reaction stages arranged in series and consisting each of a cylindrical reactor of steel coupled with an external recirculation system and a heat exchanger. The volume of each stage is 7.2 liters.

There is introduced, continuously, into the recirculation system of the first stage: 1 kg/h of a $C_4$ cut having the following composition:
  butane and isobutane: 23.5%
  isobutene: 12.0%
  1-butene: 22.9%
  2-trans butene: 23.2%
  2-cis butene: 18.4%
2.8 g/h of dichloroethylaluminum dissolved in isohexane and 0.78 g/h of $C_8$ nickel carboxylate having a 10% metal content, as a solution in isohexane. The pressure in the reactor is maintained at 5 bars by continuous withdrawal of the reaction product and the temperature at 42° C. by controlling the water flow rate through the exchanger.

A portion of the n-butenes and the isobutene is converted to oligomer compounds, essentially dimers, codimers, trimers and cotrimers as well as polymers.

After three days of run, the conversions are stabilized in the first stage at 45% for the n-butenes and 80% for the isobutene; in the second stage at 67% for the n-butenes and 90% for the isobutene. 95% of the n-butenes are recovered as dimers, trimers, codimers and cotrimers.

EXAMPLE NO. 4

In the same apparatus as in example 3 and under the same operating conditions, there is introduced, at the same flow rates, the $C_4$ cut and the catalyst components, with the exception that the nickel carboxylate solution contained trifluoroacetic acid at a concentration corresponding to a flow rate of 0.15 g/h. After 3 days of operation, the conversion of butenes to a mixture of oligomers was stabilized at the following levels: in the first stage 67% for the n-butenes and 88% for the isobutene; in the second stage 76% for the n-butenes and 98% for the isobutene. 95% of the n-butenes were recovered as dimers, trimers, codimers and cotrimers.

EXAMPLE NO. 5

The oligomerization reactor is formed of a steel cylindrical vessel, coupled with an external recirculation system operated at a flow rate of 770 l/h and with a heat exchanger. The total reaction volume is 35 liters. There is introduced continuously into the recirculation system 5 kg/h of a $C_3$ cut containing approximately 70% by weight of propylene and 30% by weight of propane, 1.65 g/h of dichloroethylaluminum as a solution in isooctane and 0.30 g/h of nickel 2-ethyl hexanoate as a solution in isooctane further containing trichloroacetic acid at a concentration corresponding to a 0.14 g/h flow rate thereof. The pressure in the reactor is maintained at 15 bars by continuous withdrawal of the reaction product and the temperature at 42° C. by controlling the flow rate through the exchanger. These operating conditions correspond to an average residence time and a concentration of aluminum and nickel compounds identical to those of example 1.

After two days of run, the conversion of propylene to a mixture mainly consisting of dimers and trimers is stabilized at a level of 90%. The yield amounts to 97%.

EXAMPLES NOS. 6 TO 12

In the same apparatus as in example 1 and under the same operating conditions, there is introduced, at the same flow rates, a $C_3$ cut and the catalyst components except that the nickel carboxylate solution contained a Bronsted acid such as indicated in Table 1 at such a concentration that the molar ratio of the Bronsted acid to the nickel compound was equal to 1, except where differently indicated. The propylene conversion is reported in Table 1. The yield in all cases was about 97%.

TABLE 1

| EXAMPLE No. | BRONSTED ACID | PROPYLENE CONVERSION (%) |
|---|---|---|
| 6 | $CH_2F\ COOH$ | 83 |
| 7 | $CH\ Cl_2COOH$ | 86 |
| 8* | $CH_2Cl\ COOH$ | 82 |
| 9 | $CBr_3\ COOH$ | 85 |
| 10 | $CH_2\ Br\ COOH$ | 80 |
| 11 | $CH_2\ I\ COOH$ | 78 |
| 12 | $C_3F_7\ .\ COOH$ | 89 |

*In example 8, the aluminum compound was dichloroisobutylaluminum, the molar ratio: Al/Ni was 10:1 and the molar ratio:Bronsted acid/nickel compound was 2.

EXAMPLE NO. 13

58 g/h of a liquid mixture containing 11.6% by weight of ethane and 88.4% by weight of ethylene is introduced into a reactor under a pressure of 15 bars. The catalyst is introduced at a rate of 0.046 g/h of Al Et $Cl_2$, 0.013 g/h of nickel $C_8$-$C_{10}$ alkane carboxylate and trifluoracetic acid in a molar ratio of 1:1 with respect to the nickel compound. The temperature was maintained at 45° C.

98% of the ethylene was converted. There was obtained a yield of 98% by weight of a product having the following composition (by moles):

$C_4$: 46.4%
$C_6$: 29.1% (mixture of hexanes and methylpentenes)
$C_8$: 12.0%
$C_{10}$: 5.9%
$C_{12}$-$C_{16}$: 6.6%

What is claimed is:

1. A catalyst composition obtained by contacting, in any order, at least one bivalent nickel compound with at least one hydrocarbylaluminum halide of the formula $AlRCl_2$ wherein R is a monovalent hydrocarbon group, has, and at least one organic Bronsted acid whose $pK_a$ at 20° C. is at most equal to 3.

2. A catalyst composition according to claim 1, wherein the Bronsted acid is a halogeno carboxylic acid of the formula $R_1\ COOH$ wherein $R_1$ is a halogenoalkyl radical containing from 1 to 3 carbon atoms, complying with the formula $C_mH_pX_q$ wherein X is halogen, $m=1$, 2 or 3, p is zero or an integer and q is an integer, with the condition that $p+q=2m+1$.

3. A catalyst composition according to claim 2, wherein the Bronsted acid is halogeno acetic acid of the formula $R_2\ COOH$ where $R_2$ is a halogenomethyl group of the formula $CX_n\ H_{3-n}$, X being halogen and n an integer from 1 to 3.

4. A catalyst composition according to claim 3, wherein the Bronsted acid is trifluoroacetic, trichloracetic or tribromoacetic acid.

5. A catalyst composition according to claim 1, wherein the nickel compound is a nickel carboxylate of the formula $(R_3COO)_2Ni$ where $R_3$ is a hydrocarbyl radical having from 5 to 20 carbon atoms or where the two $R_3$ radicals together form alkylene radical having from 6 to 18 carbon atoms.

6. A catalyst composition according to claim 1, wherein the molar ratio of the hydrocarbylaluminum halide to the nickel compound is from 1:1 to 50:1 and the molar ratio of the Bronsted acid to the hydrocarbylaluminum halide is from 0.001:1 to 1:1.

7. A catalyst composition according to claim 1, wherein the molar ratio of the hydrocarbylaluminum halide to the nickel compound is from 2:1 to 20:1, the molar ratio of the Bronsted acid to the hydrocarbylaluminum halide is from 0.01:1 to 0.5:1 and the molar ratio of the Bronsted acid to the nickel compound is from 0.25:1 to 5:1.

8. A composition according to claim 1, wherein the nickel compound has a solubility of at least 1 g/liter in n-heptane at 20° C.

9. A catalyst composition according to claim 1, wherein said hydrocarbylaluminum halide is dichloroethylaluminum or dichloroisobutylaluminum.

* * * * *